United States Patent [19]

Burke

[11] Patent Number: 5,215,991
[45] Date of Patent: Jun. 1, 1993

[54] COMBINATION OF SELECTIVE ALPHA-ADRENERGIC AGONISTS AND NA+/H+ EXCHANGE INHIBITORS USEFUL IN LOWERING INTRAOCULAR PRESSURE

[75] Inventor: James A. Burke, Tustin, Calif.
[73] Assignee: Allergan, Inc., Irvine, Calif.
[21] Appl. No.: 633,103
[22] Filed: Dec. 20, 1990

Related U.S. Application Data

[63] Continuation of Ser. No. 470,848, Jan. 26, 1990, abandoned.

[51] Int. Cl.$^5$ ............... A61K 31/495; A61K 31/415
[52] U.S. Cl. .................................... 514/255; 514/392; 514/913
[58] Field of Search .................... 514/255, 913, 392

[56] References Cited

U.S. PATENT DOCUMENTS

| | | | |
|---|---|---|---|
| 3,890,319 | 6/1975 | Danielewicz et al. | 424/250 |
| 4,400,378 | 8/1983 | Innemee et al. | 424/244 |
| 4,515,800 | 5/1985 | Cavero et al. | 514/392 |

FOREIGN PATENT DOCUMENTS 2127167 12/1972 Fed. Rep. of Germany.

OTHER PUBLICATIONS

Rouot et al., *J. Med. Chemistry* 19(8), 1049 (1976).
Simchowitz and Cragoe, *Molecular Pharmacology* 30, 112 (1986).
Chem. Abst. 109: 32089w (1988).
Chem. Abst. 103: 68755a (1985).

*Primary Examiner*—Frederick E. Waddell
*Assistant Examiner*—Zohreh A. Fay

[57] ABSTRACT

Methods and pharmaceutical compositions of alpha$_2$ agonists and Na+/H+ exchange inhibitors which are useful in lowering intraocular pressure (IOP) and treatment of intraocular hypertension are disclosed. Co-administration of a therapeutic amount of alpha$_2$ agonist with a potentiating amount of Na+/H+ exchange inhibitor is effective in lowering IOP and treatment of intraocular hypertension.

12 Claims, 7 Drawing Sheets

COMBINATION OF SELECTIVE ALPHA-ADRENERGIC AGONISTS AND NA+/H+ EXCHANGE INHIBITORS USEFUL IN LOWERING INTRAOCULAR PRESSURE

This is a continuing application under 35 U.S.C. of U.S. Ser. No. 07/470,848, filed 26 Jan. 1990, now abandoned.

FIELD OF THE INVENTION

This invention relates to combinations of $alpha_2$ adrenoceptor agonists and Na+/H+ exchange inhibitors useful in lowering intraocular pressure.

BACKGROUND OF THE INVENTION

Glaucoma is a disease of the eye characterized by increased intraocular pressure. The intraocular pressure (IOP) in the hypertensive eye causes atrophy and excavation of the ocular nerve thereby producing the visual field defects associated with glaucoma. If untreated, increased IOP may cause blindness. It is known that IOP may be affected by application of various adrenergic agents. Adrenergic agents exert their activity by interaction with receptors (adrenoceptors). The agents may be characterized by their activity, i.e., as stimulating agents (agonists) or blocking agents (antagonists), and by the specific type of adrenoceptors upon which they act.

Adrenoceptors are of two primary types: alpha and beta. Based upon the selectivity of the receptors for a series of agonists and antagonists, the alpha adrenoceptors are divided into subtypes, designated $alpha_1$ and $alpha_2$.

Alpha agonists preferentially stimulate each type of adrenoceptor with varying degrees of specificity rather than exclusivity. Therefore selectivity for an adrenoceptor subtype is relative. Alpha agonists with relative selectivity for the $alpha_2$ subtype are efficacious in lowering IOP and are part of current ocular hypertension therapy, including glaucoma therapy. However, some undesirable side effects are associated with the use of these compounds for these indications. For example, some alpha agonists are known to cause significant and undesirable cardiovascular depression and mydriasis (pupil dilation). These side effects are mediated by central nervous system $alpha_2$ adrenoceptors and ocular $alpha_1$ adrenoceptors, respectively.

Because of this, efforts are being made to develop more selective $alpha_2$ agonists which remain localized in the ocular environment. In addition, methods and compositions are being developed which potentiate the IOP effect of the $alpha_2$ agonist allowing a reduction in dose which reduces the side effects associated with its use.

It has now been discovered that Na+/H+ exchange inhibitors, such as various amiloride analogs, e.g., 5-(N,N-hexamethylene) amiloride, 5-(N-ethyl-N-isopropyl) amiloride and 5-(N,N-dimethyl) amiloride, although substantially inactive by themselves in lowering IOP, improve the ocular hypotensive profile of various $alpha_2$ agonists when co-administered with the $alpha_2$ agonist. Co-administering a Na+/H+ exchange inhibitor mitigates, reduces or eliminates undesirable side effects associated with conventional $alpha_2$ agonist therapy for treatment of ocular hypertension by enabling treatment with lower $alpha_2$ agonist dosages. In addition, co-administration of an $alpha_2$ agonist with a Na+/H+ exchange inhibitor enables equivalent or improved therapeutic treatment of ocular hypertension as compared to using equivalent or higher dosages of the $alpha_2$ agonist alone.

SUMMARY OF THE INVENTION

The invention relates to the discovery that co-administrating an $alpha_2$ agonist with a potentiating amount of Na+/H+ exchange inhibitor lowers intraocular pressure (IOP) and is useful in the treatment of ocular hypertension.

The present invention relates to a method for lowering intraocular pressure (IOP) comprising co-administrating to the eye of a mammal suffering from ocular hypertension an effective amount of an $alpha_2$ agonist and a potentiating amount of a Na+/H+ exchange inhibitor.

The present invention further relates to an ophthalmically acceptable formulation for lowering intraocular pressure (IOP) comprising an effective amount of an $alpha_2$ agonist and a potentiating amount of a Na+/H+ inhibitor.

DETAILED DESCRIPTION OF THE INVENTION

Co-administration refers to administering compounds of the present invention serially, or at substantially the same time or simultaneously. Co-administration includes administering the compounds of the present invention separately but at substantially the same time, or administering them at the same time in one pharmaceutical preparation. Serial administration includes administering the compounds of the present invention one after the other wherein the time between administration of the compounds is about one hour or less.

An ophthalmically acceptable formulation refers to a formulation comprising an $alpha_2$ agonist and a Na+/H+ exchange inhibitor in a suitable carrier of one or more ophthalmically suitable excipients.

Alpha2 agonist, as used herein, refers to compounds that preferentially stimulate $alpha_2$ adrenoceptors and exchange inhibitor, as used herein, refers to compounds which preferentially inhibit Na+/H+ exchange.

Potentiating effect, resulting from co-administration of an ophthalmically acceptable formulation comprising an $alpha_2$ agonist and a Na+/H+ exchange inhibitor, refers to decreasing the time for onset of hypotensive effect of the combination, decreasing or eliminating the unwanted initial hypertensive activity of $alpha_2$ agonists which occurs in some mammals but is not observed in humans, increasing the hypotensive effect over that observed using an $alpha_2$ agonist alone, or reducing side effects associated with $alpha_2$ agonists by enabling use of relatively smaller dosages of an $alpha_2$ agonist in the treatment of ocular hypertension.

The $alpha_2$ agonists of the present invention exhibit hypotensive activity in lowering IOP. It is contemplated that any $alpha_2$ agonist which exhibits ocular hypotensive activity can be used in this invention. The preferred $alpha_2$ agonist of the present invention are derived from imidazolidines and their tautomers.

Preferred imidazolidine-derived $alpha_2$ agonists of the present invention are represented by the tautomeric formulae below:

wherein

I. $R_1$ and $R_2$ independently are $C_{1-6}$ alkyl, fluoro, chloro, bromo, or trifluoromethyl; and one of $R_3$ and $R_4$ is hydrogen and the other is selected from hydroxy, —N($R_5,R_7$), —COOR$_3$, —CO—N($R_5,R_6$), —NR$_5$COR$_6$, —CH$_2$OH, —CN, —OH, —OCOR$_8$, —COCH$_3$, —C(CH$_3$)NOH, —CHNOH, wherein $R_5$ and $R_6$ independently are hydrogen or $C_{1-6}$ alkyl, $R_7$ is hydrogen, $C_{1-6}$ alkyl, 2-hydroxyethyl, 2-hydroxypropyl or 3-hydroxypropyl, $R_8$ is $C_{1-6}$ alkyl; or II. $R_1$ is $C_{1-6}$ alkyl, fluoro, chloro, bromo or trifluoromethyl; $R_2$ is hydrogen; $R_3$ is selected from hydroxy, —N($R_9,R_{10}$), and —NR$_9$COR$_9$; and $R_4$ is hydrogen, $C_{1-6}$ alkyl, fluoro, chloro, bromo or trifluoromethyl, wherein $R_9$ is hydrogen or $C_{1-6}$ alkyl, $R_{10}$ is hydrogen, $C_{1-6}$ alkyl, 2-hydroxymethyl, 2-hydroxypropyl or 3-hydroxypropyl, or III. $R_1$ and $R_2$ can have any of the above meanings, and $R_3$ and $R_4$ together is a fused benzene ring (to form a quinoline derivative), or a fused piperazine ring (to form a quinoxaline derivative);

or a pharmaceutically acceptable salt thereof. The alkyl substituents may be straight or branched chained. The preferred alkyl substituents are methyl and ethyl derivatives.

The preparation of most of the imidazolidine-derived compounds described above is disclosed in one or more of the following references which are incorporated herein in their entirety: *Clonidine and Related Analouges, Quantitative Correlations*, B. Rouot, et al., *J. Med. Chem.*, Vol. 19, No. 8, 1049–54 (1976); U.S. Pat. No. 4,515,800 to Cavero, et al.; and U.S. Pat. No. 3,890,319 to Danielowicz, et al. Other imidazolidine-derived compounds described above may be made using techniques and skills well known in the art.

The most preferred imidazolidine-derived alpha$_2$ agonist compounds are clonidine, p-aminoclonidine and 5-bromo-6-(2-imidazolidine-2-ylamino)quinoaxaline.

Other alpha$_2$ agonists, such as those derived from azepins, more specifically 2-amino-6-alkyl-4,5,7,8-tetrahydro-6H-thiazolo-(5,4-d) azepine and 2-amino-6-ethyl-4,5,7,8-tetrahydro-6H-oxazolo-(5,4-d) azepin may be used herein without departing from the scope of the present invention.

The preparation of these azepine-derived compounds is disclosed in one or more of the following references which are incorporated herein in their entirety: *Oxazolo and Thiazolo Derivatives for Glaucoma Treatment*, K. Thomas, G.m.b.H., Jpn. Kokai Tokyo Koho JP 58 46,092 (83 46,092) 17 Mar. 1983; and Offenlegungsschrift 2,127,267 (14 Dec. 1972) Bundesrepublik Deutschland.

Other alpha$_2$ agonists, such as derived from phenylethylamines, more specifically epinephrine, norepinephrine and dipivalylepinephrine, may be used herein without departing from the scope of the present invention. Preparation of epinephrine, norepinephrine and dipivalylepinephrine are known in the art and they are readily and commercially available.

It is expected that any Na$^+$/H$^+$ exchange inhibitor can be used in this invention. The preferred Na$^+$/H$^+$ exchange inhibitors are derived from amiloride. More preferred are various amiloride analogs, e.g., 5-(N,N-hexamethylene) amiloride, 5-(N-ethyl-N-isopropyl) amiloride and 5(N-ethyl-n-isopropyl) amiloride and 5(N,N-dimethyl) amiloride, and the pharmaceutically acceptable salts thereof.

The preparation of amiloride and its analogs is disclosed in the following reference which is incorporated herein in its entirety: Belgian Patent No. 639,386 (Merck).

Potentiating the ocular hypotensive effect of an alpha$_2$ agonist by co-administrating an alpha$_2$ agonist and a Na$^+$/H$^+$ exchange inhibitor to a hypertensive eye may focus on one or more aspects of treatment of ocular hypertension, depending on the needs or goals of the treatment and/or management of the patient's ocular hypertension. Potentiating effects include, but are not limited to, decreasing the time for onset of hypotensive effect, decreasing any hypertensive effects, increasing the hypotensive effect of alpha$_2$ agonist, both in a dose responsive manner and over time, and decreasing the side effects which may be associated with the use of the alpha$_2$ agonist while maintaining an equivalent therapeutic effect by decreasing the amount of alpha$_2$ agonist used in combination with the Na$^+$/H$^+$ exchange inhibitor.

Doses of alpha$_2$ agonist in an ophthalmic preparation effective, non-toxic amount of the agonist in a pharmaceutically acceptable liquid, gel, cream or an aqueous or nonaqueous liquid suspension or solution. In this regard, the preferred effective dose range of alpha$_2$ agonist having a therapeutic effect in mammals is from about 0.001% to about 1.0% weight/volume. Regardless of the preferred range stated herein, one can determine the most efficacious dose for a particular alpha$_2$ agonist by carrying out a dose response curve as is well known in the art.

Doses of Na$^+$/H$^+$ exchange inhibitor in ophthalmic preparations within the scope of the present invention will comprise an effective, non-toxic potentiating amount of a Na$^+$/H$^+$ exchange inhibitor.

Therapeutically effective doses of an alpha$_2$ agonist and a Na$^+$/H$^+$ exchange inhibitor will vary depending on what therapeutic effect is desired or the special needs and idiosyncrasies of the individual patient. Accordingly, a wide range of alpha$_2$ agonist/Na$^+$/H$^+$ exchange inhibitor dose ratios are possible. Preferably, the dose ratio of alpha$_2$ agonist/Na$^+$/H$^+$ exchange inhibitor is about 0.00005/1 to about 100/1. The most preferred dose ratio of alpha$_2$ agonist/Na$^+$/H$^+$ exchange inhibitor is about 0.025/1 to about 100/1. It is possible to determine precise therapeutic dose ratios by carrying out a dose response curve as is well known in the art.

In this regard, the preferred dose of Na$^+$/H$^+$ exchange inhibitor having an ocular hypotensive potentiating effect in mammals when co-administered with an alpha$_2$ agonist is from about 0.01% to about 2.0% weight/volume of Na$^+$/H$^+$ exchange inhibitor to solution.

Ophthalmic preparations having only an alpha$_2$ agonist or a Na$^+$/H$^+$ exchange inhibitor in the preferred dose ranges may be prepared. However, it is preferred to make ophthalmic preparations having both an alpha$_2$ agonist and a Na$^+$/H$^+$ exchange inhibitor for the convenience of the patient.

Topical ophthalmic preparations, for example ocular drops, gels or creams, are preferred because of ease of application, ease of dose delivery, and fewer systemic side effects, such as hypotension. An exemplary topical ophthalmic formulation is shown below in Table I. The abbreviation q.s. means a quality sufficient to effect the result or make volume.

TABLE I

| Ingredient | Amount (% w/v) |
|---|---|
| alpha$_2$ agonist | about 0.00001 to about 1.0 |
| Na$^+$/H$^+$ exchange inhibitor | about 0.01 to about 2.0 |
| Preservative | 0–0.10 |
| Vehicle | 0–40 |
| Tonicity Adjustor | 1–10 |
| Buffer | 0.01–10 |
| pH Adjustor | q.s. pH 4.5–7.5 |
| Antioxidant | as needed |
| Purified Water | as needed to make 100% |

Various preservatives may be used in the ophthalmic preparation described in Table I above. Preferred preservatives include, but are not limited to, benzalkonium chloride, chlorobutanol, thimerosal, phenylmercuric acetate, and phenylmercuric nitrate. Likewise, various preferred vehicles may be used in the ophthalmic preparation of the present invention. These vehicles include, but are not limited to, polyvinyl alcohol, povidone, hydroxypropyl methyl cellulose, poloxamers, carboxymethyl cellulose, hydroxyethyl cellulose, and purified water.

Tonicity adjustors may be added as needed or convenient. They include, but are not limited to, salts, particularly sodium chloride, potassium chloride, mannitol, and glycerin, or any other suitable ophthalmically acceptable tonicity adjustor.

Various buffers and means for adjusting pH may be used so long as the resulting preparation is ophthalmically acceptable. Accordingly, buffers include, but are not limited to, acetate buffers, citrate buffers, phosphate buffers, and borate buffers. Acids or bases may be used to adjust the pH of these formulations as needed.

An ophthalmically acceptable antioxidant for use in the present invention includes, but is not limited to sodium metabisulfite, sodium thiosulfate, acetylcysteine, butylated hydroxyanisole, and butylated hydroxytoluene.

Other excipient components which may be included in the exemplary ophthalmic preparation described in Table I are chelating agents which may be added as needed. The preferred chelating agent is edetate disodium, although other chelating agents may also be used in place of or in conjunction with it.

A useful formulation for an ophthalmic preparation comprising the present invention is shown below in Table II.

TABLE II

| Ingredient | Amount (% w/v) |
|---|---|
| alpha$_2$ agonist | about 0.0001 |
| Na$^+$/H$^+$ exchange inhibitor | about 0.01 to about 2.0 |
| Benzalkonium Chloride | 0–0.10 |
| Polyvinyl Alcohol (Grade 20-90) | 0–40 |
| Sodium Chloride | 1–10 |
| Sodium Citrate, Dihydrate | 0.01–10 |
| Citric Acid, Monohydrate | 0.01–2 |
| Purified Water | q.s. to make 100% |

EXPERIMENTAL

Ocular co-administration of an alpha$_2$ agonist and a Na$^+$/H$^+$ exchange inhibitor to effect lowering of IOP was experimentally tested in the New Zealand White rabbit. In the experimental model, co-administrating an alpha$_2$ agonist and a Na$^+$/H$^+$ exchange inhibitor demonstrated significant potentiation of the ocular hypotensive effect of the alpha$_2$ agonist.

The effect of co-administrating of alpha$_2$ agonists and a Na$^+$/H$^+$ exchange inhibitor on lowering IOP was testing in New Zealand White rabbits with normotensive IOP and weighing 3–4 kg. Topical anesthesia was produced by instillation of about 5 μl of 0.05%.

Separate solution of various alpha$_2$ agonists and a Na$^+$/H$^+$ exchange inhibitor were prepared by dissolving the specified quantity of agonists or the Na$^+$/H$^+$ exchange inhibitor in distilled water to obtain the concentrations shown below in Table III. The pH of the final solutions ranged from about 4 to about 7.5 as indicated by the characteristics of the individual drugs.

TABLE III

| | Concentration (% w/v) |
|---|---|
| Alpha Agonist | |
| Clonidine | 0.1 |
| p-aminoclonidine | 0.1 |
| 5-bromo-6-(2-imidazolidine-2-ylamino)quinoxaline | 0.1; 0.01; 0.001 |
| Na$^+$/H$^+$ exchange inhibitor | 0.1; 0.3; 1 |
| 5(N-ethyl-N-isopropyl) amiloride | |

The animals were divided into 2 groups. One group was treated with the Na$^+$/H$^+$ exchange inhibitor followed by an alpha$_2$ agonist and the other group received vehicle followed by the alpha$_2$ agonist. Intraocular pressure (IOP) was measured in both eyes for each animal using a calibrated DIGILAB® pneumatonograph. Immediately following the baseline reading for each animal, 50 μl of the Na$^+$/H$^+$ exchange inhibitor solution or vehicle was instilled into the lower conjunctival sac of the test eye of the animal, with the contralateral eye receiving 50 μl of saline in the lower conjunctival sac as a control. Thirty minutes after application of the Na$^+$/H$^+$ exchange inhibitor or vehicle, IOP was again measured for the eye. Immediately following these measurements, 50 μl of one of the alpha$_2$ agonists solution given in Table III was administered to the test eye in the same manner described above. Thereafter, IOP measurements for each eye of each animal were made at 30 minutes after administration of the alpha$_2$ agonist, then hourly for 6 hours. In separate experiments, the IOP response to the Na$^+$/H$^+$ exchange inhibitor alone was determined.

Figure 1A:
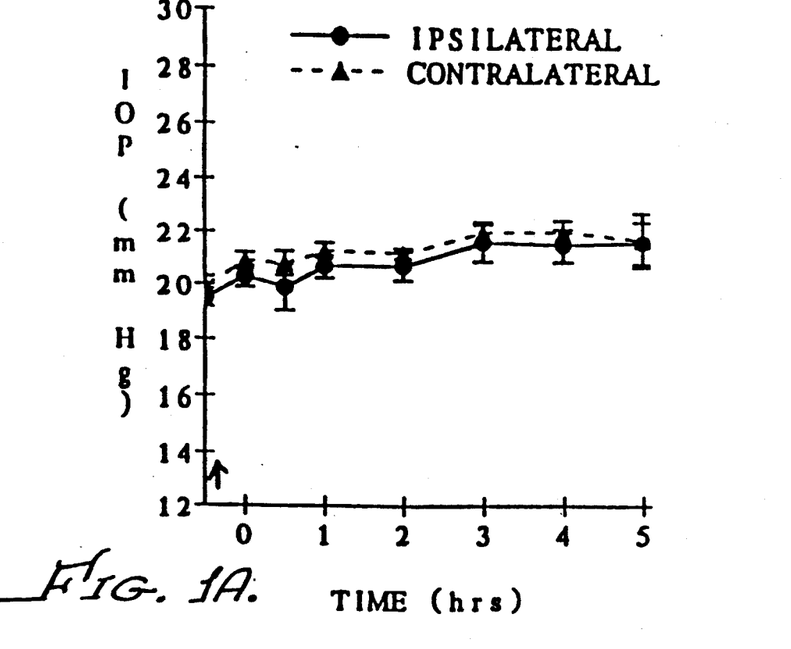
Figure 1B:
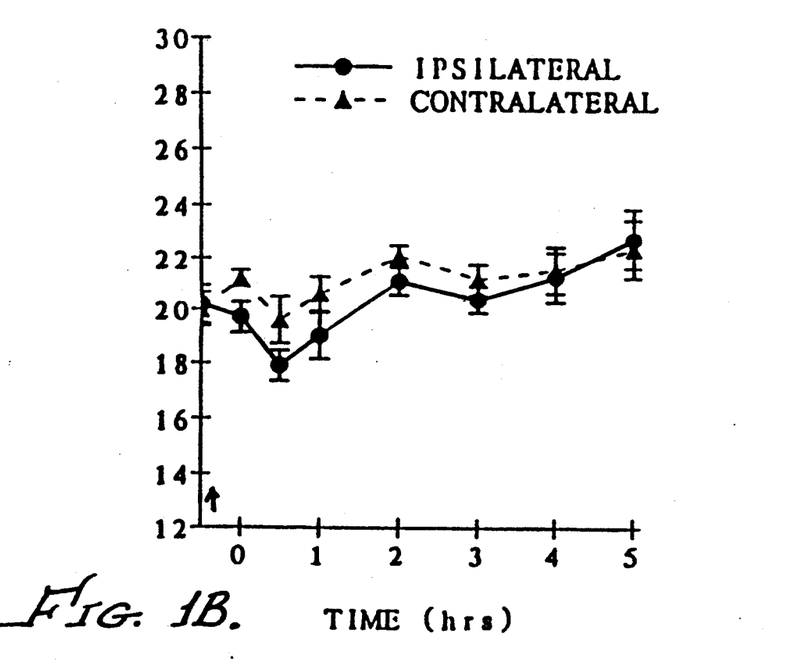
Figure 1C:
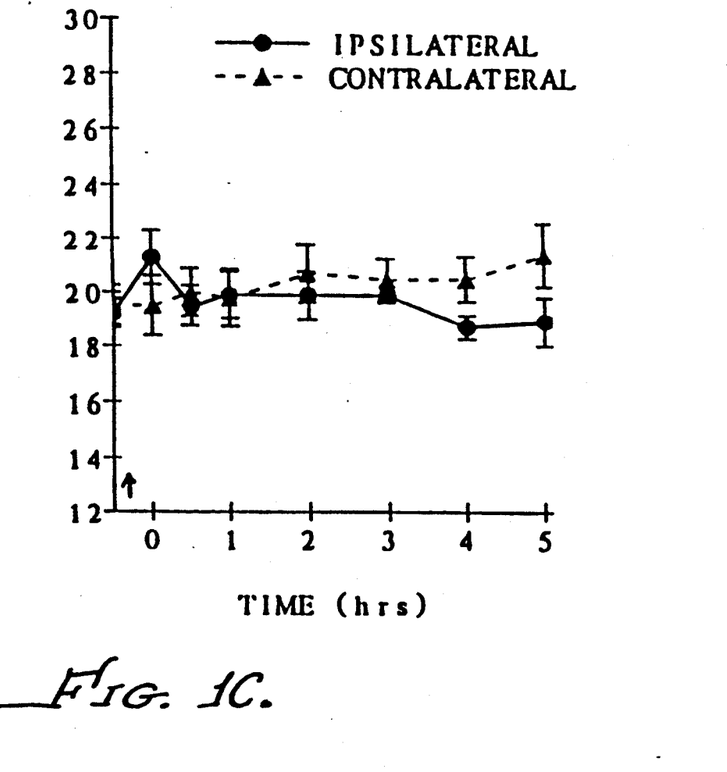
Figure 2A:
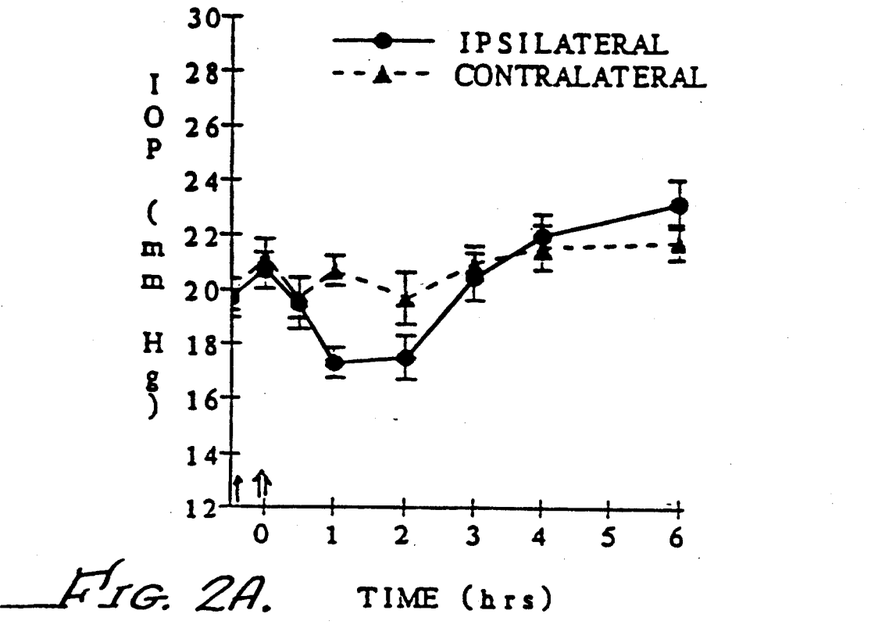
Figure 2B:
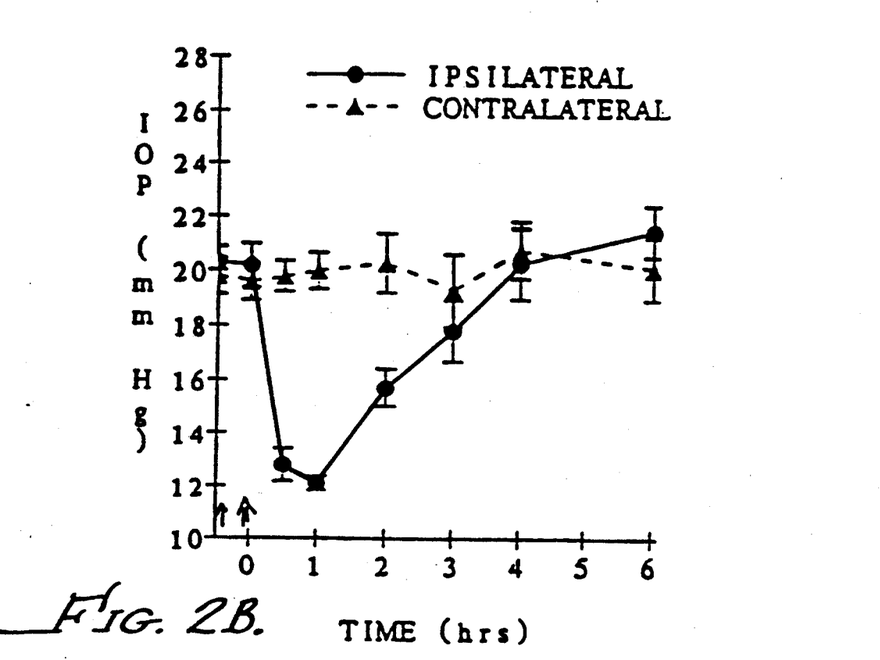
Figure 2C:
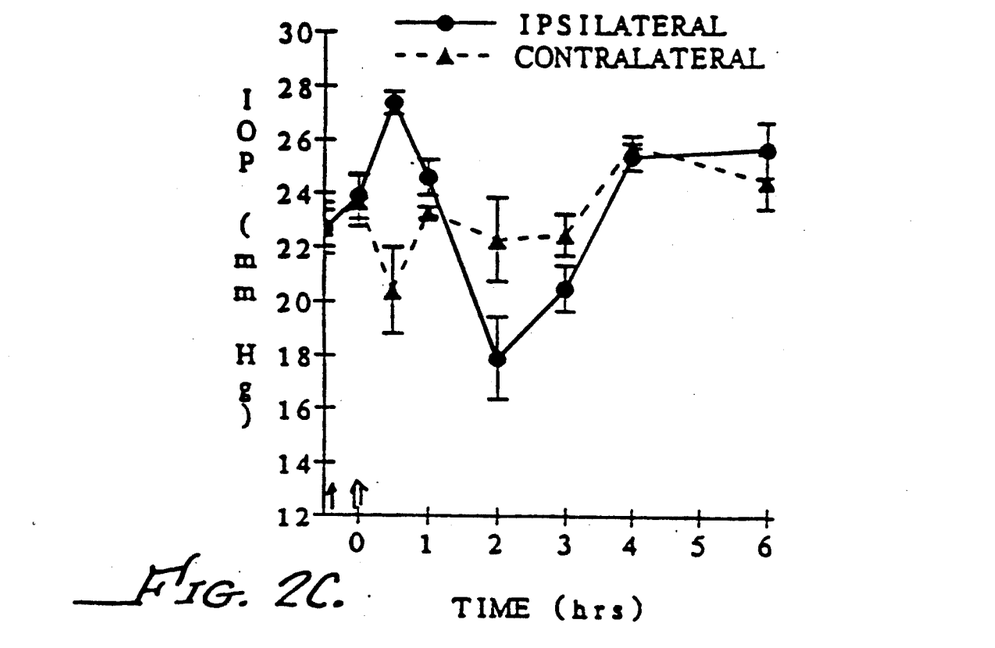
Figure 2D:
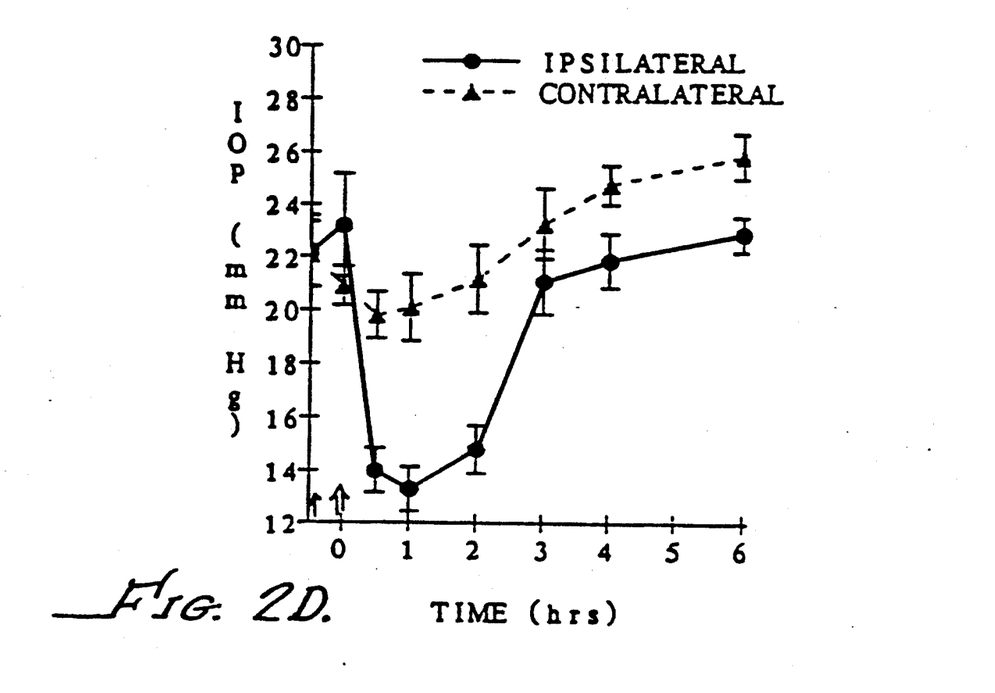
Figure 2E:
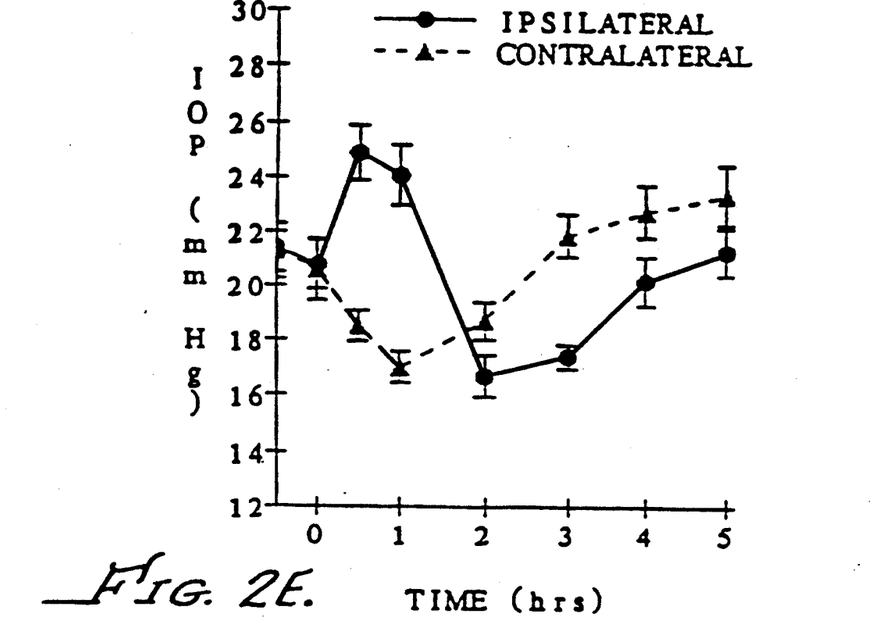
Figure 2F:
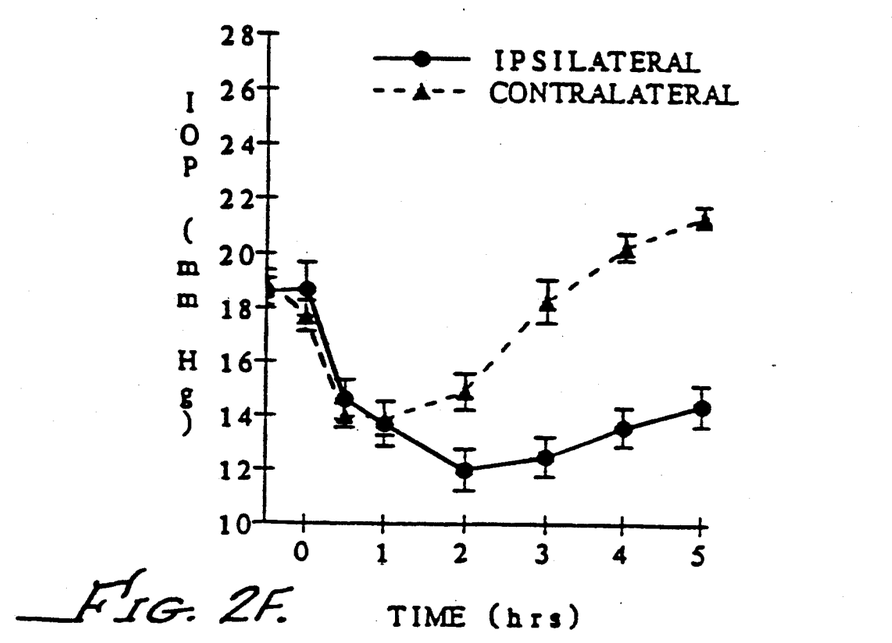

The experimental results are illustrated in FIGS. 1–4. Administration of three concentrations (0.1, 0.3, 1%) of the Na$^+$/H$^+$ exchange inhibitor did not significantly alter IOP (FIG. 1). Pretreatment with the Na$^+$/H$^+$ exchange inhibitor (1%) augmented the ocular hypotensive response to 5-bromo-6-(2-imidazolidine-2-ylamino) quinoxaline (FIG. 2A, B, C), clonidine (FIG.

Figure 3A:
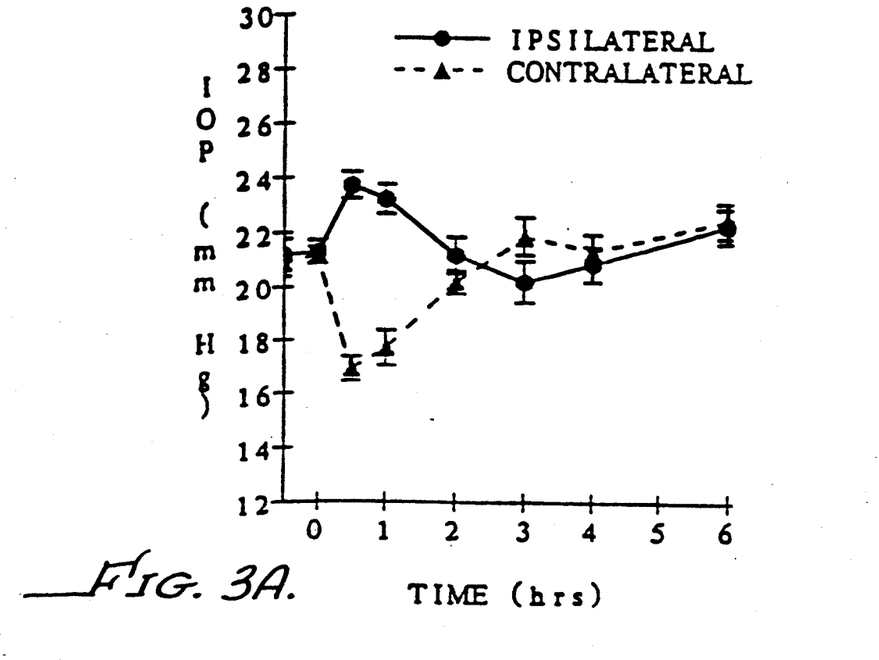
Figure 3B:
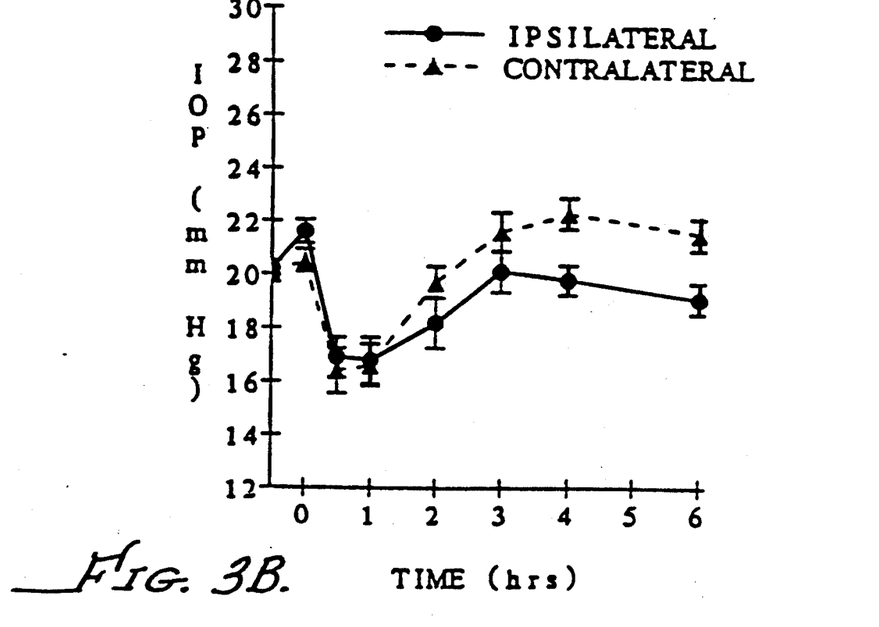
Figure 4A:
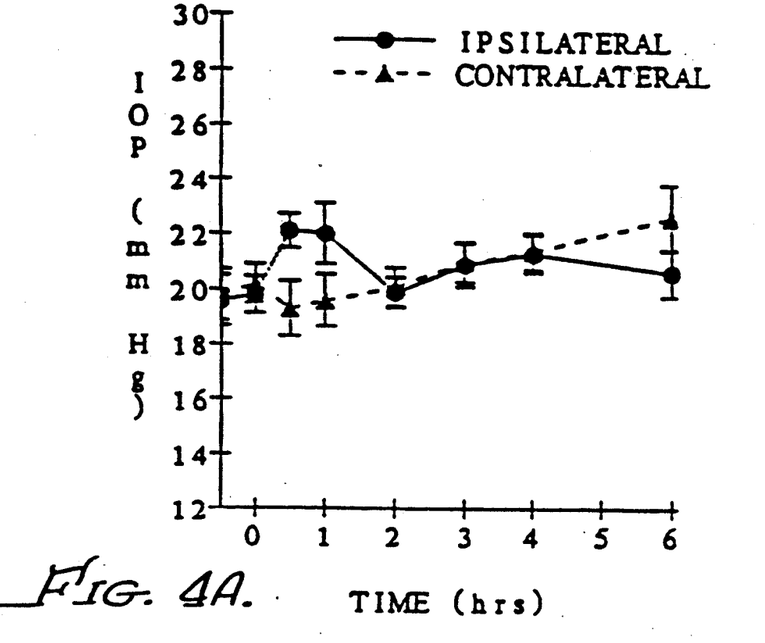
Figure 4B:
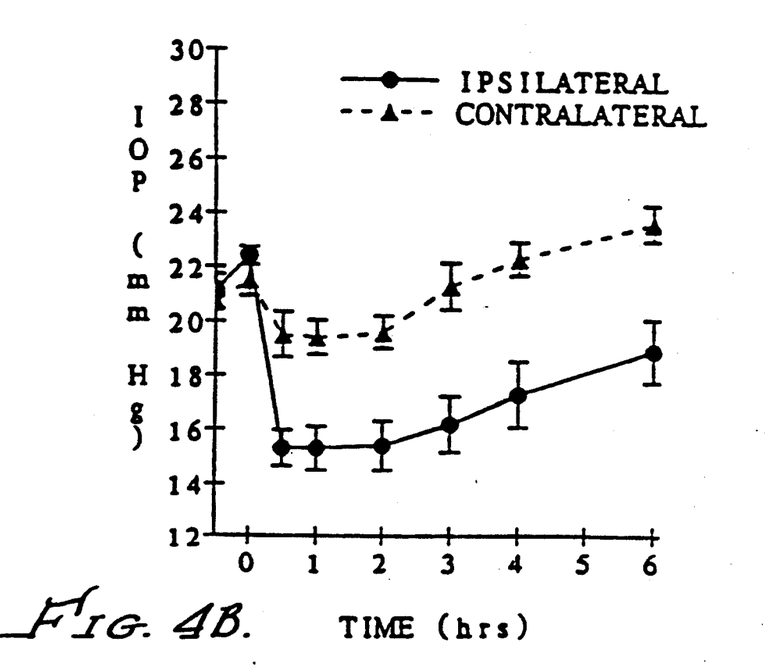

3) and p-amino clonidine (FIG. 4). The results of these experiments demonstrated that the IOP lowering effect of the alpha$_2$ agonists was potentiated by co-administration of the Na$^+$/H$^+$ exchange inhibitor.

EXAMPLE 2

In another series of experiments, carried out in substantially the same manner as set forth in Example 1, various amiloride analogs with varying potencies at inhibiting Na$^+$/H$^+$ exchange were co-administered with an alpha$_2$ agonist, p-amino clonidine, and IOP determine. The amiloride analogs are listed in ascending order of potencies at inhibiting Na$^+$/H$^+$ exchange (Table IV). Table V and Table VI set forth the results of these experiments at 1 hour and 3 hours post p-amino clonidine administration, respectively. The data are expressed as mean changes from pre-drug levels. The amiloride analogs did not change IOP when administered alone. The data show a positive correlation between inhibition of Na$^+$/H$^+$ exchange and the decrease in IOP caused by co-administration of amiloride analogs and p-amino clonidine.

TABLE IV

| Na$^+$/H$^+$ exchange inhibitor | Ki (μM)* |
|---|---|
| 5-(N,N-hexamethylene) amiloride | 0.16 |
| 5-(N-ethyl-N-isopropyl) amiloride | 0.36 |
| 5-(N,N-dimethyl) amiloride | 6.9 |
| Amiloride | 83.8 |

*Data taken from Inhibition of Chemotactic Factor-Activated Na$^+$/H$^+$ Exchange in Human Neutrophils by Analogues of Amiloride: Structure-Activity Relationships in the Amiloride Series, L. Simchowitz and E. Cragoe, Jr. Molecular Pharmacology, Vol. 30, p. 112–120, 1986.

TABLE V

| | ΔIOP (mmHg) at 1 Hr. | | |
|---|---|---|---|
| Na$^+$/H$^+$ exchange inhibitor | p | (X + p) | (X + p) − p |
| 5-(N,N-hexamethylene) amiloride | +3.0 | −8.6 | −11.6 |
| 5-(N-ethyl-N-isopropyl) amiloride | +3.0 | −7.2 | −10.2 |
| 5-(N,N-dimethyl) amiloride | +3.0 | +1.8 | −1.2 |
| Amiloride | +3.1 | +3.0 | +0.2 |

X = Na$^+$/H$^+$ inhibitor (1%)
p = p − amino clonidine (0.1%)

TABLE VI

| | ΔIOP (mmHg) at 3 Hr. | | |
|---|---|---|---|
| Na$^+$/H$^+$ exchange inhibitor | p | (X + p) | (X + p) − p |
| 5-(N,N-hexamethylene) amiloride | +2.6 | −7.5 | −10.1 |
| 5-(N-ethyl-N-isopropyl) amiloride | +1.7 | −5.7 | −7.4 |
| 5-(N,N-dimethyl) amiloride | +2.6 | +0.7 | −1.9 |
| Amiloride | +2.0 | +2.6 | +0.6 |

X = Na$^+$/H$^+$ inhibitor (1%)
p = p − amino clonidine (0.1%)

These data demonstrate that the serial co-administration of Na$^+$/H$^+$ exchange inhibitors and the alpha$_2$ agonists (30 minutes later) resulted in a substantial and significant lowering of IOP over treatment with only the alpha$_2$ agonists.

The foregoing description details specific methods and compositions that can be employed to practice the present invention, and represents the best mode contemplated. However, it is apparent for one of ordinary skill in the art that further combinations with the desired pharmacological properties can be found and administered in an analogous manner. Thus, however detailed the foregoing may appear in the text, it should not be construed as limiting the overall scope hereof; rather, the ambit of the present invention is to be governed only by the lawful construction of the appended claims.

What is claimed:

1. A method for lowering intraocular pressure (IOP) comprising co-administering to the eye of a mammal an effective IOP lowering amount of an alpha$_2$ agonist and a potentiating amount of the Na$^+$/H$^+$ exchange exhibitor, amiloride or its analogs.

2. A method according to claim 1, wherein the ratio of alpha$_2$ agonist to amiloride or its analogs is from about 0.00005/1 to about 100/1.

3. A method according to claim 2, wherein the ratio of alpha$_2$ agonist to amiloride or its analogs is from about 0.025/1 to 25/1.

4. A method according to claim 1, wherein said alpha$_2$ agonist is an imidazolidine derivative.

5. A method according to claim 4, wherein said imidazolidine derivative is selected from the group consisting of clonidine, p-aminoclonidine and 5-bromo-6-(2-imidazolidine-2-ylamino)quinoxaline.

6. A method according to claim 1, wherein said amiloride or its analogs is selected from the group consisting of 5-(N,N-hexamethylene)amiloride, 5-(N-ethyl-N-isopropyl)amiloride and 5-(N,N-dimethyl)amiloride.

7. An ophthalmically acceptable composition for lowering intraocular pressure (IOP) comprising an effective, IOP lowering amount of alpha$_2$ agonist and a potentiating amount of amiloride or its analogs.

8. A composition according to claim 7, wherein the ratio of alpha$_2$ agonist to amiloride or its analogs is from about 0.00005/1 to about 100/1.

9. A composition according to claim 7, wherein the ratio of alpha$_2$ agonist to amiloride or its analogs is from about 0.025/1 to 25/1.

10. A composition according to claim 7, wherein said alpha$_2$ agonist is an imidazolidine derivative.

11. A composition according to claim 10, wherein said imidazolidine derivative is selected from the group consisting of clonidine, p-aminoclonidine and 5-bromo-6-(2-imidazolidine-2-ylamino)quinoxaline.

12. A composition according to claim 7, wherein said amiloride or its analogs is selected from the group consisting of 5-(N,N-hexamethylene)amiloride, 5-(N-ethyl-N-isopropyl)amiloride and 5-(N,N-dimethyl)amiloride.

* * * * *